(12) United States Patent
Sheth et al.

(10) Patent No.: US 6,625,489 B2
(45) Date of Patent: Sep. 23, 2003

(54) DYNAMIC NON-COMPETITIVE ATRIAL PACING

(75) Inventors: Nirav Vijay Sheth, Coon Rapids, MN (US); Robert A. Betzold, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 12 days.

(21) Appl. No.: 09/929,617

(22) Filed: Aug. 14, 2001

(65) Prior Publication Data

US 2003/0036777 A1 Feb. 20, 2003

(51) Int. Cl.$^7$ .................................. A61N 1/368

(52) U.S. Cl. ............................ 607/9; 607/14

(58) Field of Search ........................ 607/4–25

(56) References Cited

U.S. PATENT DOCUMENTS

| | | | |
|---|---|---|---|
| 5,273,035 A | | 12/1993 | Markowitz et al. ........... 607/14 |
| 5,342,405 A | * | 8/1994 | Duncan |
| 5,374,280 A | | 12/1994 | den Dulk ..................... 607/14 |

* cited by examiner

*Primary Examiner*—Scott M. Getzow
(74) *Attorney, Agent, or Firm*—Girma Wolde-Michael

(57) ABSTRACT

The invention is directed to pacing techniques designed to avoid competitive atrial pacing. In particular, the techniques dynamically adjust a non-competitive atrial pacing (NCAP) interval based on sensed cardiac conditions. An apparatus capable of delivering pacing stimuli, such as a pacemaker or an implantable cardioverter/defibrillator (ICD), is described that inhibits delivery of an atrial pacing stimulus for an NCAP interval having a duration that is adjusted according to sensed cardiac conditions. The apparatus may adjust the duration of the NCAP interval when sensing, for example, premature ventricular contraction (PVC), pacemaker mediated tachycardia (PMT), or atrial arrhythmia (AA).

37 Claims, 5 Drawing Sheets

DYNAMIC NON-COMPETITIVE ATRIAL PACING

FIELD

The invention relates to medical devices, and more particularly, to medical devices that deliver pacing stimuli to a heart.

BACKGROUND

A pacemaker is an electronic medical device that is used to selectively stimulate a heart with electrical pulses in order to assist the heart in circulating blood. A pacemaker may be an external device connected to the body using electrodes, but more commonly is an implanted device operating from internal batteries or via an inductive link to an external power source.

Depending upon the disease or malfunction of the heart, the pacemaker delivers pacing pulses to the atrium, the ventricles, or both, in the case of dual chamber pacemakers. By monitoring electrical activity sensed from the heart, the pacemaker determines the intrinsic rhythm of the heart, and provides stimulation pulses that force depolarization of the atrium, ventricles, or both, at appropriate times to stabilize the electrical rhythm of the heart.

Some dual chamber pacemakers are designed to avoid "competitive atrial pacing" (CAP) that may arise when the pacemaker delivers an atrial pacing pulse (AP) within the natural refractory period of the atrium. In such a situation, the atrial stimulus may either fail to achieve atrial capture, or may induce an atrial arrhythmia, including atrial fibrillation and atrial flutter. In addition, the actual interval between atrial and ventricular depolarizations of the heart will be prolonged beyond the desired AV interval. Other potential undesired effects include sustaining or even accelerating an existing atrial arrhythmia, or causing general confusion caused by the delivery of an atrial pacing pulse during an existing arrhythmia.

Consequently, some conventional dual chamber pacemakers can operate in a non-competitive atrial pacing (NCAP) mode designed to prevent competitive atrial pacing. When operating in NCAP mode, conventional pacemakers delay atrial stimuli by a pre-defined interval, referred to herein as the NCAP interval, to avoid pacing during the natural refractory period of the atrium. In some pacemakers, the interval is typically a fixed interval of, for example, 300 milliseconds. Other pacemakers support a manually adjusted interval that may be set by a clinician or other operator within a pre-determined operating range, such as between 200 milliseconds and 400 milliseconds.

Similar techniques are illustrated by Markowitz et al., U.S. Pat. No. 5,273,035, that describes a dual chamber pacing technique in which the atrial stimuli is delayed from early atrial signals to avoid atrial competition. Similarly, den Dulk, U.S. Pat. No. 5,374,280, describes a dual chamber pacemaker that identifies an early atrial sense event within a post-ventricular atrial refractory interval (PVARP), and inhibits delivery of the atrial stimuli for a predetermined interval following the occurrence of such an atrial sense event.

SUMMARY

In general, the invention is directed to pacing techniques designed to avoid competitive atrial pacing. In particular, the techniques dynamically adjust a non-competitive atrial pacing (NCAP) interval based on sensed cardiac conditions. An apparatus capable of delivering pacing stimuli, such as a pacemaker or an implantable cardioverter/defibrillator (ICD), uses a relatively short NCAP interval under most conditions. Under other conditions, in which the atrium may be more vulnerable to initiation of atrial arrhythmia or other undesired effects, the apparatus may use a longer NCAP interval for one or more cardiac cycles.

In one embodiment, the invention provides a method comprising detecting an atrial signal during an atrial refractory period, calculating a duration based on a sensed cardiac condition, and inhibiting delivery of an atrial pacing stimulus for an interval of the calculated duration.

In another embodiment, the invention provides an apparatus comprising a pulse generator that delivers atrial pacing stimuli to a heart, and a set of sense amplifiers that produce output signals responsive to cardiac signals received from the heart. A controller calculates a duration based on the output signals of the amplifiers, and inhibits delivery of the atrial pacing stimuli for an interval of the calculated duration upon detecting an atrial signal during an atrial refractory period.

The invention offers many advantages. For example, a fixed NCAP interval having a relatively short duration, such as 300 milliseconds as used in many conventional pacemakers, may not be sufficient to prevent competitive atrial pacing and subsequent triggering of atrial arrhythmia under certain cardiac conditions. By dynamically adjusting the NCAP interval based on sensed cardiac activity, the invention reduces the risk of competitive atrial pacing under these conditions, thereby avoiding triggering atrial arrhythmia including atrial fibrillation and atrial flutter. In addition, the dynamic NCAP interval may reduce the risk of sustaining or even accelerating an existing atrial arrhythmia, and may alleviate any general confusion caused by the delivery of an atrial pacing pulse during an existing arrhythmia.

Another advantage over the prior art includes the elimination of the need for a clinician or other operator to program a fixed NCAP interval having a long duration in an attempt to avoid competitive atrial pacing. In particular, a fixed NCAP interval having a long duration tends to limit the rate at which pacing stimuli can be applied, and may also negatively impact the synchronous operation of a dual chamber pacing system. By dynamically adjusting the NCAP interval, the invention avoids such limitations.

The above summary of the invention is not intended to describe every embodiment of the invention. The details of one or more embodiments of the invention are set forth in the accompanying drawings and the description below. Other features, objects, and advantages of the invention will be apparent from the description and drawings, and from the claims.

DETAILED DESCRIPTION

Figure 1:
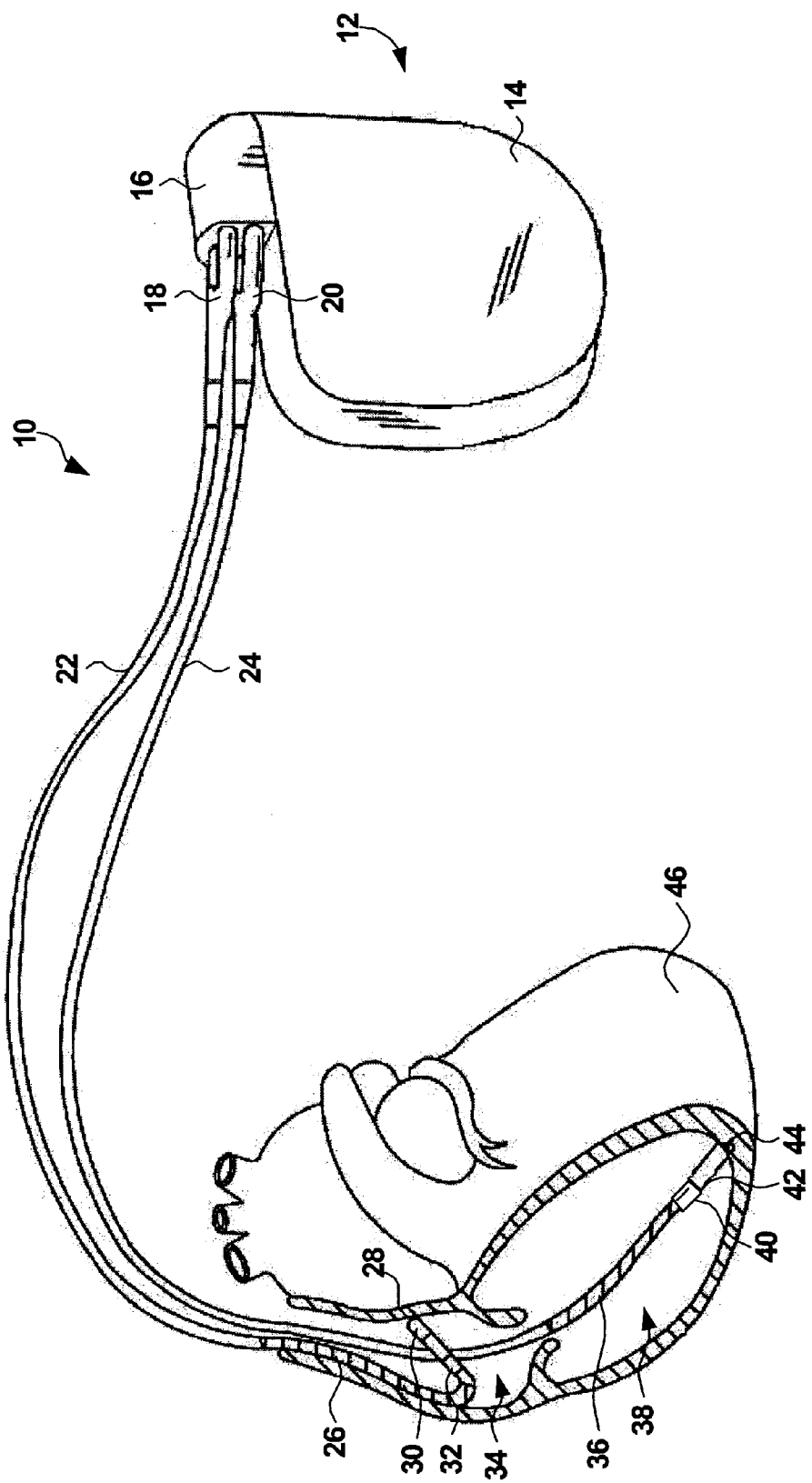
FIG. 1 illustrates an implantable dual chamber, rate responsive ICD and lead system that dynamically adjust a non-competitive atrial pacing (NCAP) interval based on sensed cardiac conditions.

FIG. 1 illustrates a dual-chamber, rate responsive implantable cardioverter/defibrillator (ICD) and lead system 10 that dynamically adjust a non-competitive atrial pacing (NCAP) interval based on sensed cardiac conditions. In particular, ICD 12 dynamically calculates a duration for the NCAP interval based on sensed cardiac conditions. Upon detecting an atrial signal during a post-ventricular atrial refractory period, ICD 12 inhibits delivery of an atrial pacing stimulus for an NCAP interval of the calculated duration. In this manner, ICD 12 avoids a triggering of atrial arrhythmia including atrial fibrillation and atrial flutter. In addition, ICD 12 may reduce the risk of sustaining or even accelerating an existing atrial arrhythmia, and may alleviate any general confusion caused by the delivery of an atrial pacing pulse during an existing arrhythmia.

Although illustrated and discussed as a pacing ICD, the invention is not limited to the exemplary device or system shown in FIG. 1, but may be practiced in a wide variety of device implementations, such as any internal or an external system delivering pacing stimuli. In addition, although described in reference to a dual-chamber pacing system, various embodiments of the invention may be used with other pacing techniques, or even with a dual-chamber pacing system operating in single-chamber pacing mode.

System 10 comprises a ventricular lead, which includes elongated insulative lead body 24, carrying three concentric coiled conductors separated from one another by tubular insulative sheaths. The distal end of the ventricular lead is deployed in right ventricle 38. Located adjacent the distal end of the ventricular lead are ring electrode 40, extendable helix electrode 44, mounted retractably within insulative electrode head 42, and elongated (approximately 5 cm) defibrillation coil electrode 36. Defibrillation electrode 36 may be fabricated from many materials, such as platinum or platinum alloy. Each of the electrodes is coupled to one of the coiled conductors within lead body 24.

Electrodes 40 and 44 are employed for ventricular pacing and for sensing ventricular depolarizations. At the proximal end of the ventricular lead is bifurcated connector 20 that carries three electrical connectors, each coupled to one of the coiled conductors.

The atrial/superior vena cava (SVC) lead includes elongated insulative lead body 22, carrying three concentric coiled conductors, separated from one another by tubular insulative sheaths, corresponding to the structure of the ventricular lead. The distal end of the atrial/SVC lead is deployed in right atrium 34. Located adjacent the distal end of the atrial/SVC lead are ring electrode 32 and extendable helix electrode 28, mounted retractably within insulative electrode head 30. Each of the electrodes is coupled to one of the coiled conductors within lead body 22. Electrodes 28 and 32 are employed for atrial pacing and for sensing atrial depolarizations. Accordingly, electrodes 28 and 32 serve as sensors for an A-EGM.

Elongated coil electrode 26 is provided proximal to electrode 32 and coupled to the third conductor within the lead body 22. Electrode 26 preferably is 10 cm in length or greater and is configured to extend from the SVC toward the tricuspid valve. At the proximal end of the lead is a bifurcated connector 18, which carries three electrical connectors, each coupled to one of the coiled conductors.

Implantable ICD 12 is shown in combination with the leads, with lead connector assemblies 18 and 20 inserted into connector block 16. Optionally, insulation of the outward facing portion of housing 14 of ICD 12 may be provided using a plastic coating, e.g., parylene or silicone rubber. However, the outward facing portion may instead be left uninsulated, or some other division between insulated and uninsulated portions may be employed. The uninsulated portion of the housing 14 optionally serves as a subcutaneous defibrillation electrode, used to defibrillate either the atria or ventricles.

Using techniques well-known in the art, ICD 12 may sense a number of different cardiac conditions based on cardiac signals received from heart 46 from a ventricular lead and an atrial lead located in right ventricle 38 and right atrium 34, respectively. ICD 12 may detect, for example, pacemaker mediated tachycardia (PMT), which is an operational pacing state in which ICD 12 erroneously stimulates ventricle 38 of heart 46 at a dangerously high rate for sustained periods. In addition, ICD 12 may detect a premature ventricular contraction (PVC), which is a ventricular activation that occurs within a normal intrinsic rhythm without an intervening atrial activation. PVC is a common cause of PMT, and typically occurs when the connective tissue between the atria and ventricles can transmit retrograde electrical signals from the ventricles to the atria. Other examples of cardiac conditions sensed by ICD 12 include atrial arrhythmia, including atrial flutter and atrial fibrillation.

As explained in detail below, when sensing such cardiac conditions, ICD 12 dynamically calculates a duration for the NCAP interval. ICD 12 may, for example, provide single chamber or dual chamber pacing stimuli using a relatively short NCAP interval under most conditions. Upon detecting the above described conditions, and other conditions at which the atria may be more vulnerable to initiation of atrial arrhythmia or other undesired effects, ICD 12 increases the NCAP interval for one or more cardiac cycles.

In particular, ICD 12 may increases the NCAP interval from a default value of 300 milliseconds to an extended value of 400 milliseconds or more upon detecting such a condition. In one embodiment, ICD 12 maintains the increased NCAP interval for a single cardiac cycle upon detecting a premature ventricular contraction (PVC). Similarly, ICD 12 may maintain the increased NCAP interval for a single cardiac cycle upon sensing a pacemaker mediated tachycardia (PMT). In addition, ICD may implement other conventional responses, such as increasing a post-ventricular atrial refractory interval (PVARP) for a single cardiac cycle in like manner. Upon detecting atrial arrhythmia, ICD 12 may increase the NCAP interval from the default value to the extended value, and maintain the extended NCAP interval until termination of the atrial arrhythmia has been detected.

Figure 2:
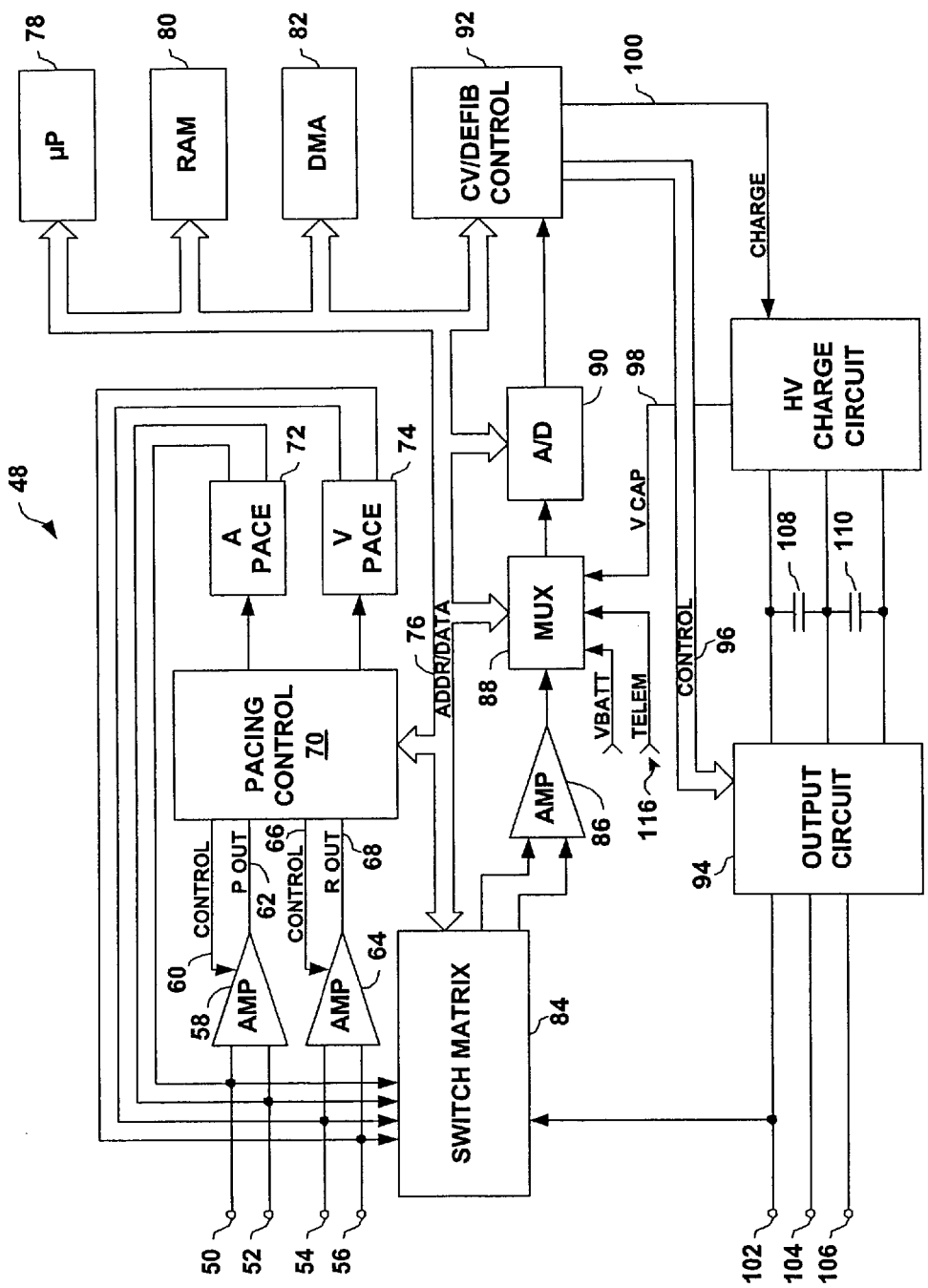
FIG. 2 is a schematic diagram illustrating an exemplary circuitry for controlling an ICD according to the principles of the invention.

FIG. 2 is a schematic diagram illustrating an exemplary circuitry 48 for controlling an implantable ICD according to the principles of the invention. The invention is not limited to the exemplary circuitry shown in FIG. 2, but may be practiced in a wide variety of device implementations, including an external pacing system.

Circuitry 48 includes a set of electrodes 50, 52, 54 and 56 for sensing cardiac signals. In particular, electrodes 54 and 56 are located on or in the ventricle, and are coupled to R-wave sense amplifier 64 that amplifies and filters cardiac signals sensed by electrodes 54 and 56. Amplifier 64 also includes a comparator that compares the cardiac signals to a pre-selected ventricular sense threshold. Based on the comparison, amplifier 64 generates an output signal on R-out line 68.

Similarly, electrodes 50 and 52 are located on or in the atrium, and are coupled to P-wave sense amplifier 58, that amplifies and filters cardiac signals sensed by electrodes 50 and 52. Amplifier 58 includes a comparator that compares the input signal to a pre-selected atrial sense threshold, which is typically different from the ventricular sense threshold. Based on the comparison, amplifier 58 generates an output signal on P-out line 62. Pacing controller 70 controls operation of amplifiers 64, 58 via control lines 66, 60, respectively.

In addition, circuitry 48 includes a number of pacing/defibrillation electrodes 102, 104 and 106 that correspond to an atrial defibrillation electrode, a ventricular defibrillation electrode and the uninsulated portion of the housing of the implantable ICD, respectively. Electrodes 102, 104 and 106 are coupled to high voltage output circuit 94 that typically includes voltage switches controlled by cardioversion/defibrillation (CV/defib) control logic 92 via control bus 96. The switches within output circuit 94 control which electrodes are employed and which are coupled to the positive and negative terminals of the capacitor bank including capacitors 108 and 110 during delivery of the defibrillation pulses.

Microprocessor 78 controls switch matrix 84 via bus 76 in order to selectively couple the electrodes to wide band (2.5–100 Hz) amplifier 86 for use in signal analysis. In particular, band-pass amplifier 86 provides the cardiac signals from the selected electrodes to multiplexer 88 and analog-to-digital (A/D) converter 90 for conversion to digital data. Direct memory access circuit 82 controls the storage of the digital data in random access memory 80 for subsequent analysis by microprocessor 78.

Pacing controller 70 and microprocessor 78 cooperate to control the operation and functionality of circuitry 48. In particular, pacing controller 70 includes programmable digital counters that control the basic time intervals associated with DDD, VVI, DVI, VDD, AAI, DDI and other modes of single and dual chamber pacing. Microprocessor 78 analyzes the digital data received from A/D converter 90 and, based on the digital data, controls the durations of these intervals.

According to the principles of the invention, microprocessor 78 dynamically calculates a duration for the NCAP interval based on cardiac signals provided by electrodes 50, 52, 54 and 56. Upon detecting an atrial signal (AS) during a natural refractory period of the atrium, microprocessor 78 directs pacing controller 70 to inhibit delivery of an atrial pacing stimulus for an NCAP interval of the calculated duration. In this manner, circuitry 48 avoids a triggering of atrial arrhythmia including atrial fibrillation and atrial flutter. In addition, circuitry 48 may reduce the risk of sustaining or even accelerating an existing atrial arrhythmia, or alleviate any general confusion by the clinician as to the purpose of delivering an atrial pacing pulse during an existing arrhythmia. Although illustrated for exemplary purposes as separate components, pacing controller 70 and microprocessor 78 may be integrated into a single component, collectively referred to as a "controller" for circuitry 48.

In addition, pacing controller 70 also controls escape intervals associated with anti-tachyarrhythmia pacing in both the atrium and the ventricle, employing any of a number of anti-tachyarrhythmia pacing therapies. Other intervals typically defined by pacing controller 70 include: atrial and ventricular pacing escape intervals; the refractory periods during which sensed P-waves and R-waves are ineffective to restart timing of the escape intervals; and the pulse widths of the pacing pulses. As with the NCAP interval, the durations of these intervals are determined by microprocessor 78, in response to stored data in memory 80 and are communicated to pacing controller 70 via address/data bus 76. Pacing controller 70 also determines the amplitude of the cardiac pacing pulses under control of microprocessor 78.

Pacing controller 70 typically resets the internal escape interval counters upon sensing of P-waves and R-waves as indicated by a signals on lines 62 and 68, and in accordance with the selected mode of pacing on time-out trigger generation of pacing pulses by pacer output circuitry 72 and 74, which are coupled to electrodes 50, 52, 54 and 56. The escape interval counters are also reset on generation of pacing pulses, and thereby control the basic timing of cardiac pacing functions, including anti-tachyarrhythmia pacing. The value of the count present in the escape interval counters when reset by sensed R-waves and P-waves may be used to measure the durations of R-R intervals, P-P intervals, P-R intervals and R-P intervals, which measurements are stored in memory 80 and used to detect the presence of tachyarrhythmias.

Microprocessor 78 typically operates as an interrupt-driven device under control of a program in the form of computer-executable instructions within a storage medium, such as a read only memory. Consequently, microprocessor 78 is responsive to interrupts from pacing controller 70 corresponding to the occurrence sensed P-waves and R-waves and corresponding to the generation of cardiac pacing pulses. These interrupts are provided via data/address bus 76. In response to an interrupt, microprocessor 78 dynamically calculates the duration for the NCAP interval, and performs any other necessary mathematical calculations, and updates of the values or intervals controlled by pacing controller 70.

Using techniques well known in the art, microprocessor 78 senses a cardiac condition, and initiates an appropriate pacing regimen by calculating the corresponding timing intervals, and loading the intervals into pacing controller 70. Microprocessor 78, for example, can direct pacing controller 70 to time a post ventricular atrial refractory period (PVARP). In general, PVARP is the period following a ventricular event during which a sensed atrial signal is not used to initiate an AV interval.

Upon sensing an atrial signal during PVARP, microprocessor 78 can further direct pacing controller 70 to operate in a non-competitive atrial pacing (NCAP) mode designed to prevent competitive atrial pacing. In particular, pacing controller 70 times an NCAP interval of a duration calculated by microprocessor 78, and delays atrial stimuli for the NCAP interval. Microprocessor 78 dynamically calculates a duration for the NCAP interval based on sensed cardiac conditions. Microprocessor 78 may calculate the duration for the NCAP interval based on a number of different cardiac conditions sensed from the cardiac signals received from the electrodes. ICD 12 may adjust the NCAP interval upon detecting, for example, pacemaker mediated tachycardia (PMT), premature ventricular contraction (PVC), and atrial arrhythmia, including atrial flutter and atrial fibrillation.

Microprocessor 78 may provide dual chamber pacing stimuli using a relatively short NCAP interval under most conditions. Upon detecting the above described conditions, and other conditions at which the atrium may be more vulnerable to initiation of atrial arrhythmia or other undesired effects, microprocessor 78 increases the NCAP interval for one or more cardiac cycles.

In particular, microprocessor 78 may increases the NCAP interval from a default value of 300 milliseconds to an extended value of 400 milliseconds or more upon detecting such a condition. In one embodiment, microprocessor 78 maintains the increased NCAP interval for a single cardiac cycle upon sensing a premature ventricular contraction (PVC). Similarly, microprocessor 78 may maintain the increased NCAP interval for a single cardiac cycle upon sensing a pacemaker mediated tachycardia (PMT). In addition, microprocessor 78 may implement other conventional responses, such as increasing post-ventricular atrial refractory interval (PVARP) for a single cardiac cycle in like manner. Upon detecting atrial arrhythmia, microprocessor 78 may increase the NCAP interval from the default value to the extended value, and maintain the extended NCAP interval until termination of the atrial arrhythmia has been detected.

Dynamically adjusting the NCAP interval based on sensed cardiac conditions offers many advantages. A fixed NCAP interval having a relatively short duration, such as 300 milliseconds as used in many conventional pacemakers, may not be sufficient to prevent competitive atrial pacing and subsequent triggering of atrial arrhythmia under certain cardiac conditions. By dynamically adjusting the NCAP interval based on sensed cardiac activity, microprocessor 78 reduces the risk of competitive atrial pacing under these conditions, thereby avoiding a triggering of atrial arrhythmia including atrial fibrillation and atrial flutter. In addition, microprocessor 78 may reduce the risk of sustaining or even accelerating an existing atrial arrhythmia, or alleviate any general confusion by the clinician as to the purpose of delivering an atrial pacing pulse during an existing arrhythmia.

Another advantage over the prior art includes the elimination of the need for a clinician or other operator to program a fixed NCAP interval having a long duration in an attempt to avoid competitive atrial pacing. In particular, a fixed NCAP interval having a long duration tends to limit the rate at which pacing stimuli can be applied, and may negatively impact the synchronous operation of a dual chamber pacing system. By dynamically adjusting the NCAP interval, microprocessor 78 avoids such limitations.

Figure 3:
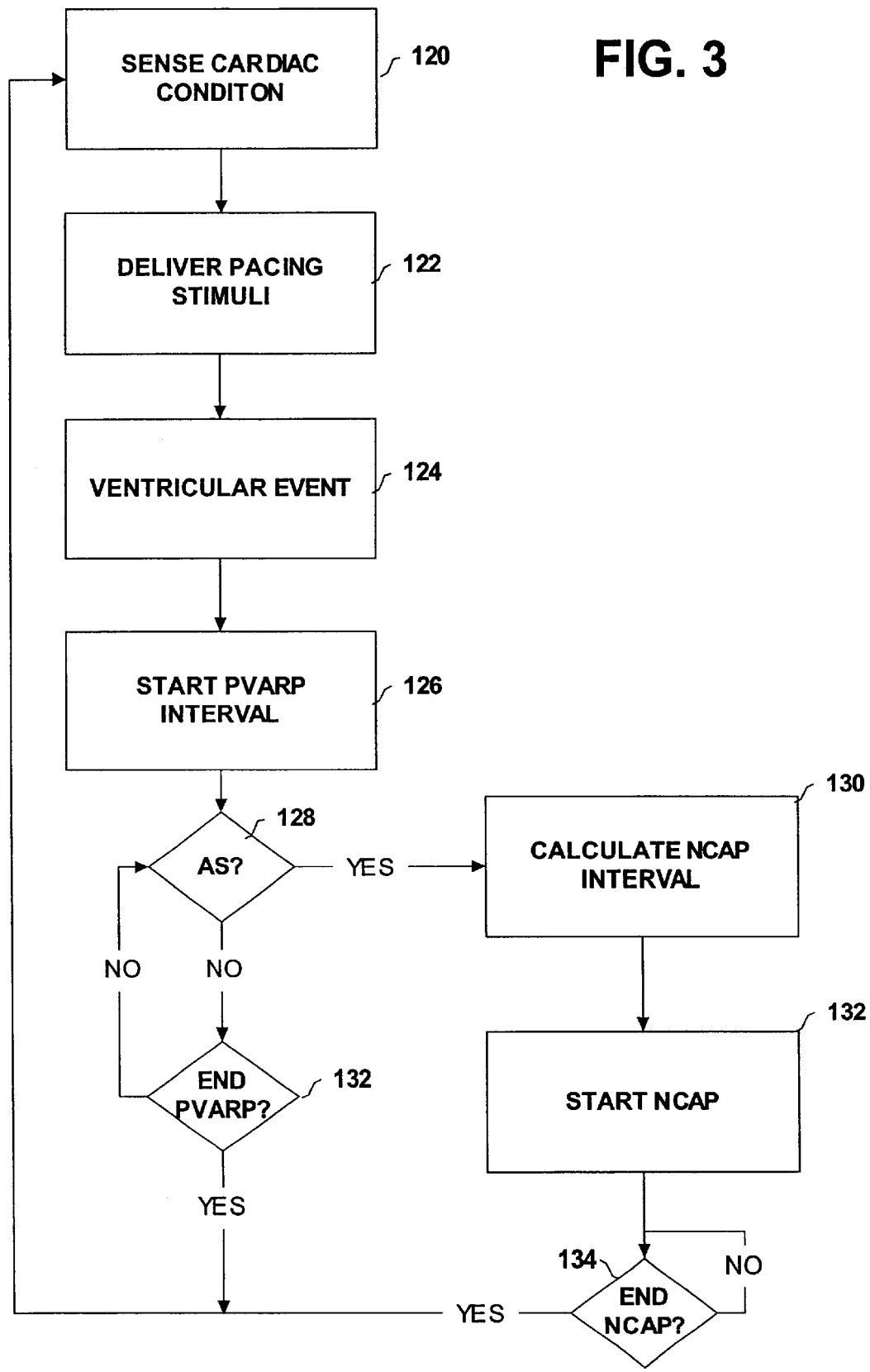
FIG. 3 is a flowchart illustrating an example mode of operation of an ICD or other pacing device that dynamically calculates a duration for the NCAP interval based on sensed cardiac conditions.

FIG. 3 is a flowchart illustrating an example mode of operation of a ICD or other pacing according to the principles of the invention. Based on a sensed cardiac condition (120), the ICD initiates an appropriate pacing regimen and delivers pacing stimuli to the heart (122). During this process, the ICD monitors for a paced or natural ventricular event (124) and initiates a post ventricular atrial refractory period (PVARP) (126).

While timing the PVARP interval, the ICD monitors sensed cardiac signals for an atrial signal (AS) during PVARP (128). Upon detecting such an event, the ICD calculates a duration for a non-competitive atrial pacing (NCAP) interval (130) and initiates the NCAP interval (132), thereby delaying subsequent atrial pacing. Upon completion of the NCAP interval (134), the ICD continues with the pacing regime. If the ICD does not detect an AS during PVARP (132), the ICD continues the pacing regime without initiating the NCAP interval.

Figure 4:
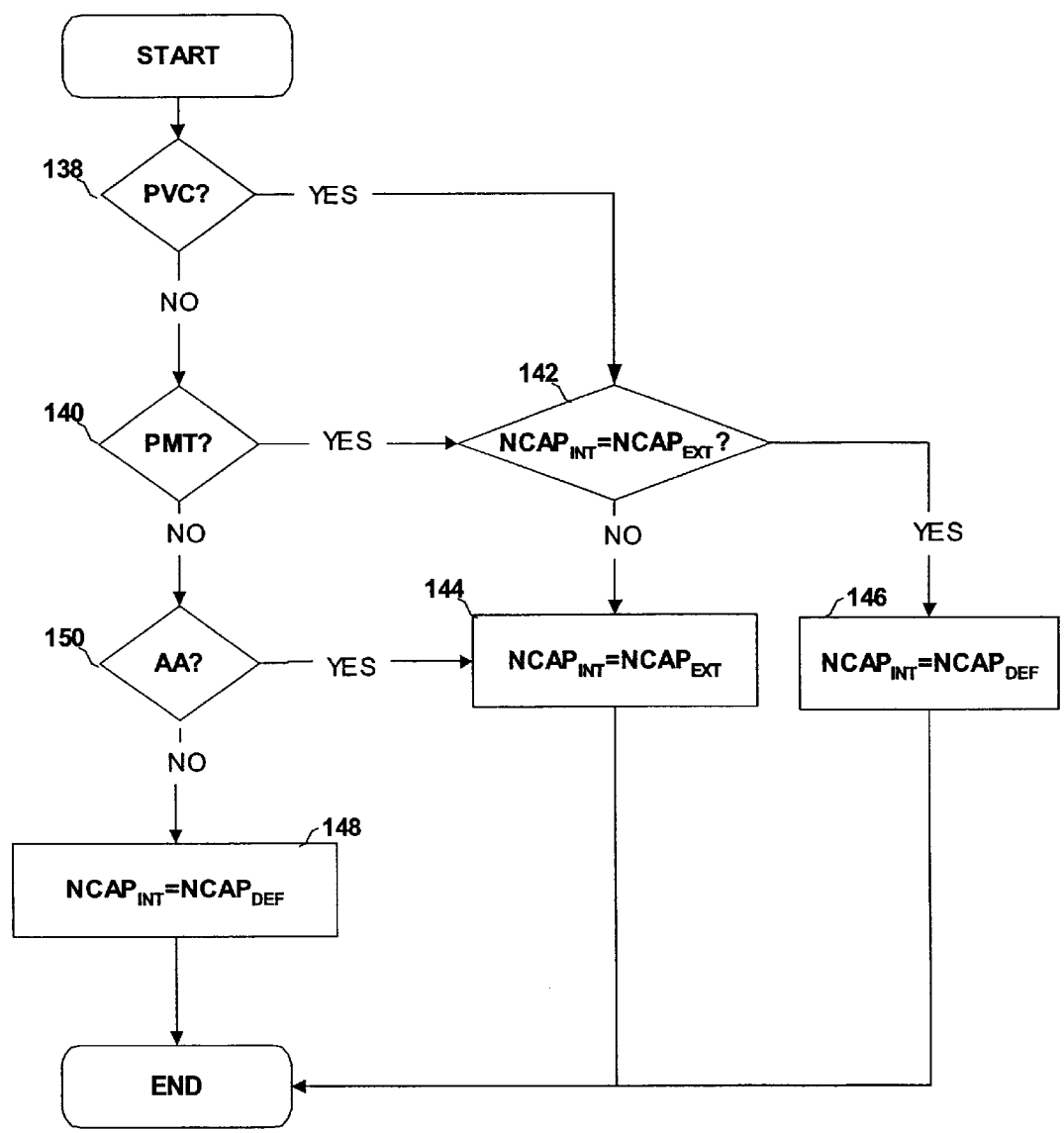
FIG. 4 is a flowchart illustrating an example process in which an ICD, pacemaker, or similar device, calculates a duration for the NCAP interval based on sensed cardiac conditions.

FIG. 4 is a flowchart illustrating one example process in which a ICD, pacemaker, or similar device, calculates a duration for the NCAP interval based on sensed cardiac conditions (step 130 of FIG. 3). In general, when an atrial signal is sensed during PVARP, the ICD sets the duration based on whether a cardiac condition has been sensed in which the atrium may be more vulnerable to initiation of atrial arrhythmia or other undesired effects. For example, in the illustrated process, the ICD determines whether the pacing regime is in response to a premature ventricular contraction (PVC) (138) or a pacemaker mediated tachycardia (PMT) (140). If so, the ICD increases the duration of NCAP interval from a default duration to an extended duration for a single cardiac cycles. In particular, the ICD determines whether the current duration for the NCAP interval ($NCAP_{INT}$) has already been increased to the extended NCAP duration ($NCAP_{EXT}$) (142). If not, the ICD sets $NCAP_{INT}$ to $NCAP_{EXT}$ (144), thereby increasing the duration of the NCAP interval. If, however, the current duration of the NCAP interval has already been increased during a previous cardiac cycle, the ICD decreases the duration of the NCAP interval by setting $NCAP_{INT}$ to a default duration ($NCAP_{DEF}$) (146).

If the ICD has not detected a PMT or a PVC, the ICD determines whether the pacing regime is in response to an atrial arrhythmia including, for example, atrial flutter and atrial fibrillation (150). If so, ICD sets $NCAP_{INT}$ to $NCAP_{EXT}$ (144) until termination of the atrial episode has been detected. If none of these cardiac conditions are present, the ICD sets the NCAP interval by setting $NCAP_{INT}$ to a default duration ($NCAP_{DEF}$). In this manner, the ICD selectively sets the NCAP duration of the NCAP interval to a first duration ($NCAP_{DEF}$) or a second duration ($NCAP_{EXT}$) based on the cardiac condition. Typical values for these durations are 300 milliseconds and 400 milliseconds for $NCAP_{DEF}$ and $NCAP_{DEF}$, respectively.

Figure 5:
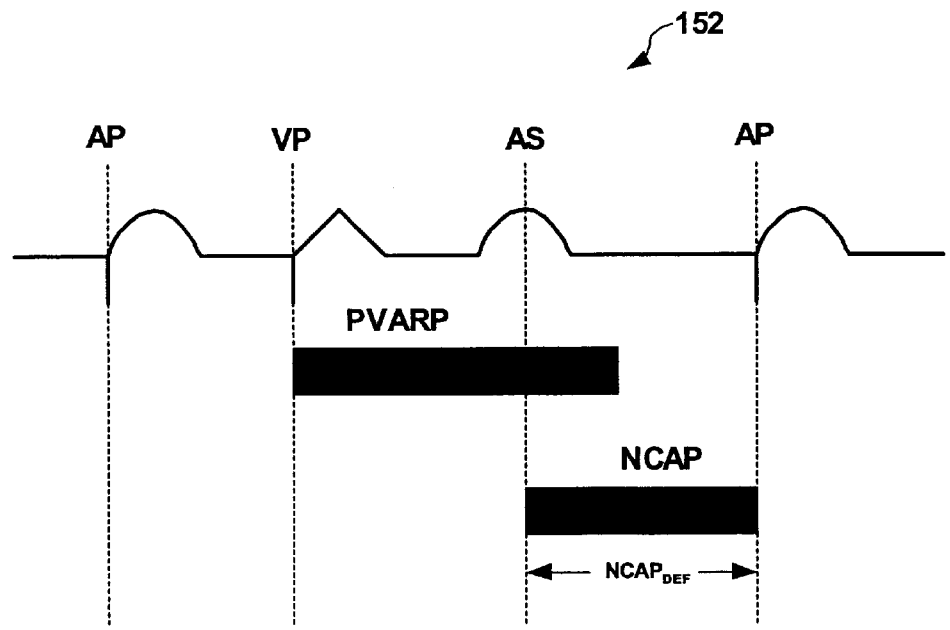
FIGS. 5 and 6 are timing diagram further illustrating the invention.

FIG. 5 is a timing diagram further illustrating the pacing techniques described herein. In particular, electrocardiogram (ECG) 152 illustrates both atrial and ventricular events and pacemaker pace pulses, and a post ventricular atrial refractory interval that is timed from the first ventricular pace pulse (VP). A sensed atrial signal (AS) during the PVARP interval initiates an NCAP interval having a calculated duration of a default value ($NCAP_{DEF}$) due to the absence of particular cardiac conditions in which the atrium is vulnerable to initiation of atrial arrhythmia or other undesired effects.

Figure 6:
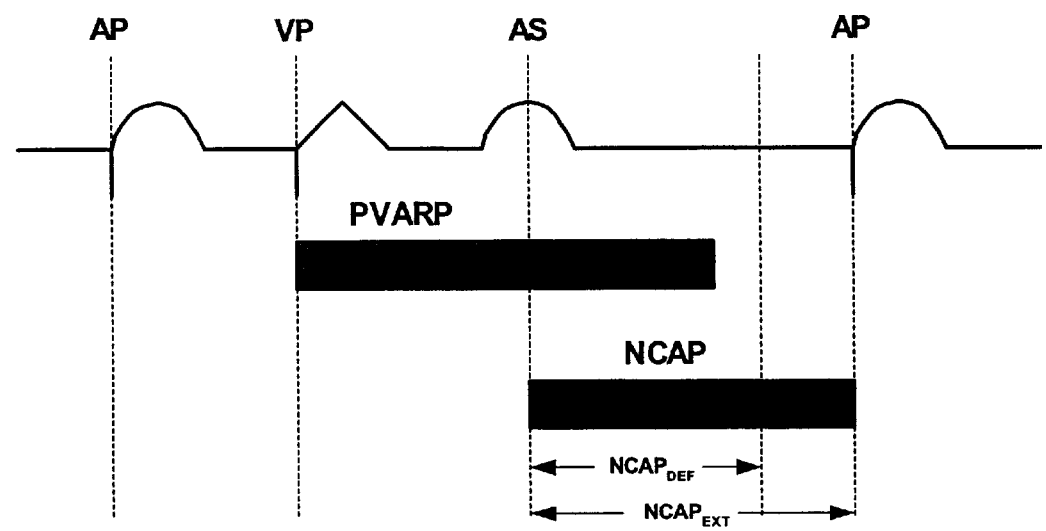

FIG. 6 is a timing diagram illustrating the situation where the ICD senses an atrial signal (AS) during the PVARP interval, and detects certain cardiac conditions such as PVC, PMT or AA. Under these conditions, NCAP is increased from $NCAP_{DEF}$ to $NCAP_{EXT}$ for one or more cardiac cycles depending on the sensed condition. As is common in conventional pacemakers, the duration of PVARP may or may not also be increased, depending on the sensed condition.

Various embodiments of the invention have been described. These embodiments are illustrative of the practice of the invention. These and other embodiments are within the scope of the following claims.

What is claimed is:

1. A method comprising:
   sensing a cardiac condition;
   detecting an atrial signal during an atrial refractory period;
   calculating a duration based on the cardiac condition; and
   inhibiting delivery of an atrial pacing stimulus for an interval of the calculated duration.

2. The method of claim 1, wherein calculating a duration comprises selectively setting the duration to a first duration or a second duration based on the cardiac condition.

3. The method of claim 1, wherein sensing a cardiac condition comprises sensing at least one of a premature ventricular contraction (PVC), pacemaker mediated tachycardia (PMT), and atrial arrhythmia (AA).

4. The method of claim 1, wherein calculating a duration comprises increasing the duration from a default duration for a single cardiac cycle.

5. The method of claim 1, wherein sensing a cardiac condition comprises sensing a premature ventricular contraction (PVC), and further wherein calculating a duration comprises increasing the duration upon sensing the PVC.

6. The method of claim 1, wherein sensing a cardiac condition comprises sensing a pacemaker mediated tachycardia (PMT), and further wherein calculating a duration comprises increasing the duration upon sensing the PMT.

7. The method of claim 1, wherein sensing a cardiac condition comprises sensing an atrial arrhythmia (AA), and further wherein calculating a duration comprises increasing the duration upon sensing the AA.

8. The method of claim 1, wherein the atrial refractory period comprises a post-ventricular atrial refractory period (PVARP).

9. A method comprising:
selectively setting a duration of an interval to:
(i) a first duration for a single cardiac cycle upon sensing a premature ventricular contraction (PVC) or a pacemaker mediated tachycardia (PMT),
(ii) a second duration upon sensing atrial arrhythmia (AA), and
(iii) a third duration in the absence of PVC, PMT and AA;
detecting an atrial signal during an atrial refractory period; and
inhibiting delivery of an atrial pacing stimulus for the interval upon detecting the ASR.

10. The method of claim 9, wherein the first duration substantially equals the second duration.

11. The method of claim 9, wherein the atrial refractory period comprises a post-ventricular atrial refractory period (PVARP).

12. A method comprising:
detecting an atrial signal during an atrial refractory period;
dynamically calculating a duration; and
inhibiting delivery of an atrial pacing stimulus from a pacemaker for an interval of the calculated duration upon detecting the atrial signal.

13. The method of claim 12, further comprising sensing a cardiac condition, wherein dynamically calculating a duration comprises dynamically calculating a duration based on the cardiac condition.

14. The method of claim 13, wherein dynamically calculating a duration comprises selectively setting the duration to a first duration or a second duration based on the cardiac condition.

15. The method of claim 13, wherein sensing a cardiac condition comprises sensing at least one of a premature ventricular contraction (PVC), pacemaker mediated tachycardia (PMT), and atrial arrhythmia (AA).

16. The method of claim 12, wherein dynamically calculating a duration comprises increasing the duration from a default duration for a single cardiac cycle.

17. The method of claim 12, wherein dynamically calculating a duration comprises selectively setting the duration to:
(i) a first duration for a single cardiac cycle upon sensing a premature ventricular contraction (PVC) or a pacemaker mediated tachycardia (PMT),
(ii) a second duration upon sensing atrial arrhythmia (AA), and
(iii) a third duration in the absence of PVC, PMT and AA.

18. An apparatus comprising:
a pulse generator to deliver atrial pacing stimuli to a heart;
a set of sense amplifiers producing output signals responsive to cardiac signals received from the heart; and
a controller that, based on the output signals of the amplifiers, calculates a duration and inhibits delivery of the atrial pacing stimuli for an interval of the calculated duration upon detecting an atrial signal during an atrial refractory period.

19. The apparatus of claim 18, wherein the controller senses a cardiac condition based on the output signals, and calculates the duration based on the cardiac condition.

20. The apparatus of claim 19, wherein the controller selectively sets the duration to a first duration or a second duration based on the cardiac condition.

21. The apparatus of claim 19, wherein the controller senses at least one of a premature ventricular contraction (PVC), pacemaker mediated tachycardia (PMT), and atrial arrhythmia (AA) based on the output signals.

22. The apparatus of claim 19, wherein the controller dynamically calculates the duration by selectively setting the duration to:
(i) a first duration for a single cardiac cycle upon sensing a premature ventricular contraction (PVC) or a pacemaker mediated tachycardia (PMT),
(ii) a second duration upon sensing atrial arrhythmia (AA), and
(iii) a third duration in the absence of PVC, PMT and AA.

23. The apparatus of claim 18, wherein the controller dynamically calculates the duration by increasing the duration from a default duration for a single cardiac cycle.

24. A pacing system comprising:
a set of electrodes to deliver atrial pacing stimuli to a heart and to sense cardiac signals from the heart; and
a pacemaker coupled to the electrodes to:
dynamically calculate a duration,
detect an atrial signal (ASR) during an atrial refractory period, and
inhibit delivery of the atrial pacing stimuli from the pacemaker for an interval of the calculated duration upon detecting the ASR.

25. The pacing system of claim 24, wherein the pacemaker senses a cardiac condition based on the cardiac signals, and dynamically calculates the duration based on the cardiac condition.

26. The pacing system of claim 25, wherein the pacemaker senses at least one of a premature ventricular contraction (PVC), pacemaker mediated tachycardia (PMT), and atrial arrhythmia (AA).

27. The pacing system of claim 24, wherein the pacemaker selectively sets the interval to a first duration or a second duration based on the cardiac signals.

28. The pacing system of claim 24, wherein the pacemaker dynamically calculates the duration by selectively setting the duration to:
(i) a first duration for a single cardiac cycle upon sensing a premature ventricular contraction (PVC) or a pacemaker mediated tachycardia (PMT)
(ii) a second duration upon sensing atrial arrhythmia (AA), and
(iii) a third duration in the absence of PVC, PMT and AA.

29. An apparatus comprising:

sense means to sense a cardiac condition;

detection means to detect an atrial signal during an atrial refractory period;

control means to calculate a duration based on the cardiac condition, and to inhibit delivery of an atrial pacing stimulus for an interval of the calculated duration upon detecting the atrial signal.

30. The apparatus of claim 29, wherein the control means selectively sets the duration to a first duration or a second duration based on the cardiac condition.

31. The apparatus of claim 29, wherein the sense means senses at least one of a premature ventricular contraction (PVC), pacemaker mediated tachycardia (PMT), and atrial arrhythmia (AA).

32. The apparatus of claim 29, wherein the control means increases the duration for a single cardiac cycle.

33. The apparatus of claim 29, wherein the atrial refractory period comprises a post-ventricular atrial refractory period (PVARP).

34. A computer-readable medium having instructions thereon for causing a processor to:

sense a cardiac condition;

detect an atrial signal during an atrial refractory period;

calculate a duration based on the cardiac condition; and inhibit delivery of an atrial pacing stimulus for an interval of the calculated duration upon detecting the atrial signal.

35. The computer-readable medium of claim 34, wherein the instructions cause the processor to selectively set the duration to a first duration or a second duration based on the cardiac condition.

36. The computer-readable medium of claim 34, wherein the instructions cause the processor to sense at least one of a premature ventricular contraction (PVC), pacemaker mediated tachycardia (PMT), and atrial arrhythmia (AA).

37. The computer-readable medium of claim 34, wherein the instructions cause the processor to increase the duration from a default duration for a single cardiac cycle.

* * * * *